United States Patent [19]

Reiser et al.

[11] 4,381,310

[45] Apr. 26, 1983

[54] ANTIMYCOTIC SUBSTITUTED 2,4-DICHLOROPHENYL-IMIDAZOLYL-VINYL-CARBINOLS

[75] Inventors: Wolf Reiser; Ludwig Elbe, both of Wuppertal; Karl H. Büchel, Burscheid; Manfred Plempel, Wuppertal, all of Fed. Rep. of Germany

[73] Assignee: Bayer Aktiengesellschaft, Leverkusen, Fed. Rep. of Germany

[21] Appl. No.: 295,276

[22] Filed: Aug. 24, 1981

[30] Foreign Application Priority Data

Sep. 9, 1980 [DE] Fed. Rep. of Germany ....... 3033917

[51] Int. Cl.$^3$ .................. A61K 31/415; C07D 233/60
[52] U.S. Cl. ............................. 424/273 R; 542/400; 542/429; 542/468; 548/341
[58] Field of Search ............... 548/341; 542/400, 429, 542/468; 424/273 R

[56] References Cited

U.S. PATENT DOCUMENTS

4,067,989 1/1978 Shephard et al. .............. 548/341 X
4,273,776 6/1981 Hoehn .............................. 548/341 X
4,277,469 7/1981 Worthington et al. ......... 548/341 X

OTHER PUBLICATIONS

March, J., *Advanced Organic Chemistry*, McGraw Hill, New York, 1968, pp. 678–681.

*Primary Examiner*—Richard A. Schwartz
*Attorney, Agent, or Firm*—Sprung, Horn, Kramer & Woods

[57] ABSTRACT

The invention relates to substituted 2,4-dichlorophenyl-imidazolyl-vinyl-carbinols of formula (I) as defined herein. The invention also includes methods for the manufacture of said compounds of formula (I), compositions containing said compounds of formula (I) and methods for the use of said compounds and compositions as antimycotic agents.

16 Claims, No Drawings

ANTIMYCOTIC SUBSTITUTED 2,4-DICHLOROPHENYL-IMIDAZOLYL-VINYL-CARBINOLS

The present invention relates to certain new substituted 2,4-dichlorophenyl-imidazolyl-vinyl-carbinol compounds, to a process for their production and to their use as antimicrobial agents, in particular as antimycotic agents.

It has already been disclosed that certain 1-phenyl-2-imidazolyl-4,4-dimethyl-1-penten-3-ols, such as 1-(4-chlorophenyl)-2-(imidazol-1-yl)-4,4-dimethyl-1-penten-3-ol, have good fungicidal properties (see DE-OS (German Published No. 2,838,847). However, the action of these compounds against fungi which are pathogenic to humans is not always completely satisfactory.

According to the present invention there are provided compounds which are substituted 2,4-dichlorophenyl-imidazolyl-vinyl-carbinols of the formula

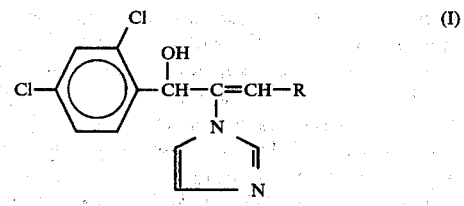

or salts thereof,
in which
R represents an alkyl radical, an optionally substituted cycloalkyl or cycloalkenyl radical, an optionally substituted cycloalkylalkyl or cycloalkenylalkyl radical, an optionally substituted alkenyl or alkinyl radical or an optionally substituted phenyl radical or a phenylalkyl radical which is optionally substituted in the alkyl part and in the phenyl part.

The compounds of the formula (I) can exist in two geometric isomer forms (E-isomer and Z-isomer), depending on the arrangement of the groups linked to the double bond; they are preferentially obtained in a varying E/Z-isomer ratio. An asymmetric carbon atom is also present, so that the compounds of the formula (I) are additionally obtained in two optical isomer forms; they are preferentially obtained in the form of racemates. The present invention relates both to the individual isomers and to the isomer mixtures.

Racemate mixtures can be separated into the pure racemates in a known manner on the basis of the physico-chemical differences of the constituents, for example by chromatography and/or fractional crystallization.

Pure racemates can be resolved according to known methods, for example by recrystallization from an optically active solvent, with the aid of microorganisms or by reaction with an optically active acid or base which forms salts with the racemic compound and separation of the salts obtained in this manner, for example on the basis of their different solubilities, into the diastereomers from which the antipodes can be liberated by the action of suitable agents. Particularly customary optically active acids are, for example, the d- and l-forms of tartaric acid, di-o-toluyltartaric acid, malic acid, mandelic acid, camphorsulphonic acid or quinic acid. Suitable optically active bases are, for example, optically active α-phenylethylamine, α-(1-naphthyl)-ethylamine, quinine, cinchonidine and brucine. Advantageously, the more active of the two antipodes is isolated.

According to the invention it is however also possible to obtain the end product in the form of pure racemates or optical antipodes by employing starting substances, containing one or more asymmetrical C atoms, in the form of the pure racemates or optical antipodes.

According to the present invention there is further provided a process for the production of a compound of the present invention, in which a 2,4-dichlorophenyl-imidazolyl-vinyl ketone of the formula

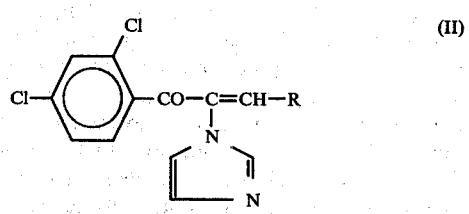

in which
R has the above-mentioned meaning, is reduced, and, if desired, the product is converted into a salt thereof.

It is furthermore possible to form derivatives on the CH(OH) group of the compounds of the formula (I), for example ether, ester and carbamoyl derivatives, in a customary and known manner.

The compounds of the present invention have powerful antimycotic properties. Surprisingly, the compounds according to the invention have an action spectrum which is generally better than the 1-phenyl-2-imidazolyl-4,4-dimethyl-1-penten-3-ols, such as, for example, 1-(4-chlorophenyl)-2-(imidazol-1-yl)-4,4-dimethyl-1-penten-3-ol, which are known from the state of the art and chemically are closely related compounds. The substances according to the invention thus represent an enrichment of pharmacy.

Preferred compounds of the present invention are those in which R represents a straight-chain or branched alkyl radical with 1 to 29, preferably to 18, carbon atoms; a cycloalkyl or cycloalkenyl radical which has in each case 5 to 7 carbon atoms and is optionally substituted by alkyl with 1 to 4 carbon atoms; a cycloalkylalkyl or cycloalkenylalkyl radical which has in each case 5 to 7 carbon atoms in the cycloalkyl or cycloalkenyl part and in each case 1 to 6 carbon atoms in the straight-chain or branched alkyl part and is optionally substituted by alkyl with 1 to 4 carbon atoms; an optionally substituted straight-chain or branched alkenyl or alkinyl radical with in each case up to 6 carbon atoms, the substituent(s) being selected from hydroxyl, alkoxy with 1 to 4 carbon atoms, and phenyl, which is optionally substituted by halogen or alkyl with 1 to 4 carbon atoms; an optionally substituted phenyl radical, substituent(s) being selected from: alkyl with 1 to 4 carbon atoms, halogenoalkyl with 1 to 2 carbon atoms and 1 to 5 identical or different halogen atoms (preferably fluorine and chlorine atoms), and phenyl and phenoxy which are optionally substituted by halogen; or an optionally substituted phenylalkyl radical with 1 to 4 carbon atoms in the alkyl part, such as, preferably benzyl and 1-phenyleth-1-yl, substituent(s) on the phenyl preferably being selected from: halogen, alkyl with 1 to 4 carbon atoms and 1 to 5 identical or different halogen atoms (preferably fluorine and chlorine atoms), and substituent(s) on the alkyl preferably being selected from cyano, hydroxycarbonyl and alkoxycarbonyl with 1 to 4 carbon atoms in the alkyl part.

Particularly preferred compounds of the present invention are those in which R represents a straight-chain or branched alkyl radical with 1 to 8 carbon atoms; an optionally methyl- or ethyl-substituted cyclohexyl, cyclohexenyl, cyclopentenyl, cyclopentyl, cyclohexylmethyl, cyclohexyl-ethyl, 2-cyclohexyl-prop-1-yl, cyclohexenyl-methyl, cyclohexenyl-ethyl or 2-cyclohexenyl-prop-1-yl radical; a methacryl, trimethylvinyl, acetylenyl, hydroxyacetylenyl, methoxyacetylenyl, phenacetylenyl, chlorophenylacetylenyl, propargyl, hydroxypropargyl, methoxypropargyl, phenylpropargyl or chlorophenylpropargyl radical; a phenyl radical which is optionally substituted by fluorine, chlorine, methyl, phenyl, phenoxy, chlorophenyl or chlorophenoxy; or a benzyl or 1-phenyl-eth-1-yl radical which is optionally substituted in the phenyl part by fluorine, chlorine or methyl, and is optionally substituted on the methyl or ethyl group, respectively, by cyano or hydroxy- or methoxy-carbonyl.

The following compounds of the formula (I) can be mentioned specifically, in addition to the compounds mentioned in the preparative Examples:

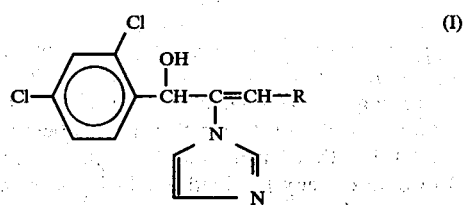

in which R denotes

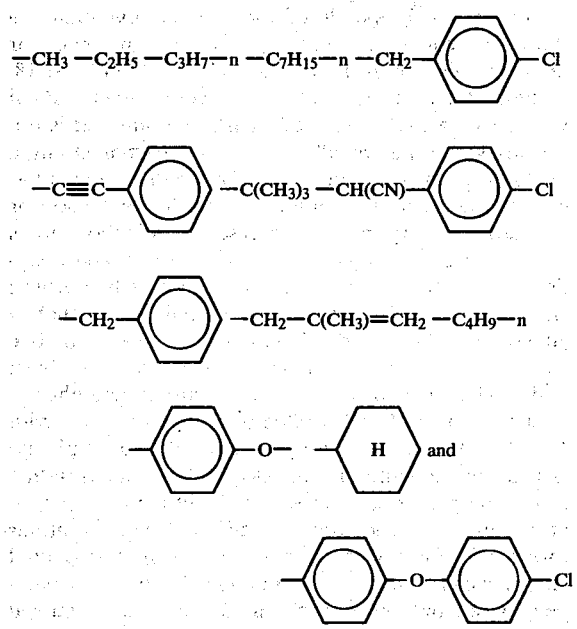

If, for example, 3-cyclohexyl-1-(2,4-dichlorophenyl)-2-(imidazol-1-yl)-2-propen-1-one and sodium borohydride are used as starting substances, the course of the reaction according to the present invention is illustrated by the following equation:

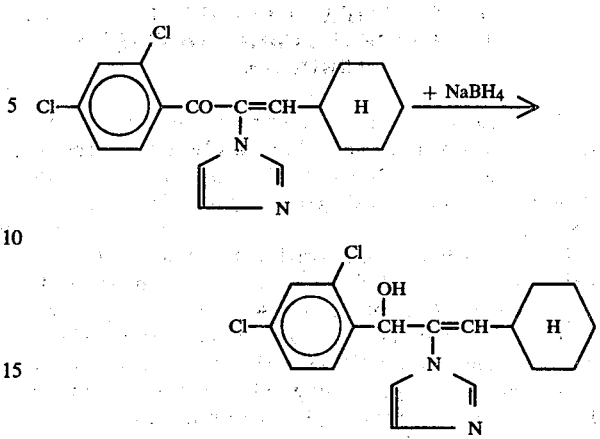

Preferred 2,4-dichlorophenyl-imidazolyl-vinyl ketones of formula (II) to be used as starting substances for the process according to the invention are those in which R represents those radicals which have already been mentioned for this substituent in connection with the description of the preferred and particularly preferred compounds according to the present invention.

The 2,4-dichlorophenyl-imidazolyl-vinyl ketones of the formula (II) are novel. However, they can be obtained as described in our copending, as yet unpublished application corresponding to German Patent Application P. No. 30 33 918.5 of Sept. 9, 1980 [Le A 20 529], by a process in which (a) a keto-enamine of the formula

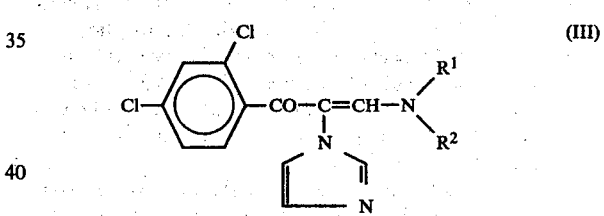

in which

R¹ and R² are identical or different and represent an alkyl radical, preferably with 1 to 4 carbon atoms, in particular a methyl radical, is reacted with an organomagnesium compound of the formula

in which

R has the above-mentioned meaning and

Hal represents a halogen atom, in particular a chlorine or bromine atom, in the customary manner, in the presence of an inert organic solvent (such as ether) and if appropriate in the presence of an inert gas (such as nitrogen) at a temperature between −20° and +120° C., or (b) 2,4-dichlorophenacyl-imidazole of the formula

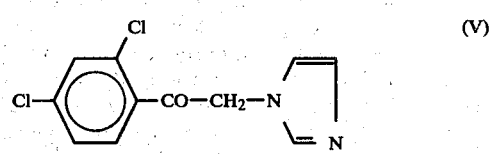

is reacted with an aldehyde of the general formula $$O=CH-R \quad \text{(VI)}$$

in which

R has the above-mentioned meaning, in the presence of an inert organic solvent (such as toluene), and in the presence of a catalyst (such as piperidine/acetic acid or benzoic acid) at a temperature between 20° and 160° C.

The keto-enamines of the formula (III) are novel; they can be obtained by a process in which 2,4-dichlorophenacyl-imidazole of the formula (V) is reacted with an amide acetal or aminal ester of the formula

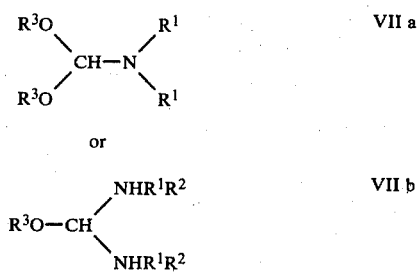

in which

R$^1$ and R$^2$ have the above-mentioned meaning and
R$^3$ represents an alkyl radical with 1 to 4 carbon atoms, in a manner which is in itself known, at the boiling point in the presence of an inert organic solvent (such as an aromatic hydrocarbon) or, preferably, in the presence of an excess of the amide acetal or aminal ester of the formula (VIIa) or (VIIb) employed (in this context, see also Chem. Ber. 101, 41–50 (1968); J. Org. Chem. 43, 4248–50 (1978) and the following preparative Examples).

The amide acetals and aminal esters of the formulae (VIIa) and (VIIb) are generally known compounds of organic chemistry (see for example, Chem. Ber. 101 41–50 (1968) and J. Org. Chem. 43, 4248–50 (1978)).

The organomagnesium compounds of the formula (IV), 2,4-dichlorophenacyl-imidazole of the formula (V) and the aldehydes of the formula (VI) are known.

The reduction according to the invention may be carried out in the customary manner, for example by reaction with complex hydrides, if appropriate in the presence of a diluent, or by reaction with aluminium isopropylate in the presence of a diluent.

If complex hydrides are used, possible diluents for the reaction according to the invention are polar organic solvents. These include, preferably, alcohols (such as methanol, ethanol, butanol or isopropanol) and ethers (such as diethyl ether, dioxane or tetrahydrofuran). The reaction is in general carried out at a temperature of −10° to +30° C., preferably at −10° to 20° C. For this reaction, generally about 1 mole of a complex hydride, such as sodium borohydride, calcium borohydride or lithium alanate, is employed per mole of the ketone of the formula (II).

To isolate the compounds of the formula (I) according to the invention, the residue is taken up in dilute hydrochloric acid and the mixture is then rendered alkaline, and extracted with an organic solvent. Further working up is effected in the customary manner.

If aluminium isopropylate is used, preferred possible diluents for the reaction according to the invention are alcohols (such as isopropanol) or inert hydrocarbon (such as benzene). The reaction temperature can again be varied within a substantial range; in general, the reaction is carried out at a temperature between 20° and 120° C., preferably at 50° to 100° C. To carry out the reaction, generally about 1 to 2 moles of aluminium isopropylate are employed per mole of the corresponding ketone of the formula (II). To isolate the compounds of the formula (I) according to the invention, the excess solvent is removed by distillation in vacuo and the aluminium compound formed is decomposed with dilute sulphuric acid or sodium hydroxide solution. Further working up is effected in the customary manner.

Among the new substituted 2,4-dichlorophenyl-imidazolyl-vinyl-carbinol salts of the invention, those salts that are pharmaceutically acceptable are particularly important and are preferred.

The new free substituted 2,4-dichlorophenyl-imidazolyl-vinyl-carbinols of the formula (I) and their salts can be interconverted in any suitable manner; methods for such interconversion are known in the art.

The following acids can preferably be used for the preparation of physiologically acceptable acid addition salts of the compounds of the formula (I): hydrogen halide acids (such as hydrobromic acid, and, preferably, in particular hydrochloric acid), phosphoric acid, nitric acid, sulphuric acid, monofunctional and bifunctional carboxylic acids and hydroxycarboxylic acids (such as acetic acid, maleic acid, succinic acid, fumaric acid, tartaric acid, citric acid, salicyclic acid, sorbic acid and lactic acid) and sulphonic acids (such as p-toluene-sulphonic acid and 1,5-naphthalene-disulphonic acid).

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manne, for example by filtration, and if appropriate purified by washing with an inert organic solvent.

The compounds of the present invention exhibit antimicrobial actions, in particular powerful antimycotic actions. They possess a very broad antimycotic action spectrum, especially against dermatophytes and blastomyces as well as bisphase fungi, for example against varieties of Candida, such as *Candida albicans*, varieties of Epidermophyton, such as *Epidermophyton floccosum*, varieties of Aspergillus, such as *Aspergillus niger* and *Aspergillus fumigatus*, varieties of Trichophyton, such as *Trichophyton mentagrophytes*, varieties of Microsporon, such as *Microsporon felineum* and varieties of Penicillium, such as *Penicillium commune*. The listing of these micro-organisms in no way implies a limitation of the germs which can be combated but is only illustrative.

Examples which may be mentioned of field of indication in medicine are: dermatomycoses and systemic mycoses, especially those caused by *Trichlohyton mentagrophytes* and other varieties of Trichophyton, varieties Microsporon, *Epidermophyton floccosum*, blastomyces and bisphase fungi as well as moulds.

As stated above, the invention also relates to the use in medicine of the Formula (I) compound of the invention.

The present invention provides pharmaceutical compositions containing as active ingredient a compound of the invention in admixture with an inert pharmaceutical carrier, e.g., a solid of liquefied gaseous diluent, or in admixture with a liquid diluent other than a solvent of a molecular weight less than 200 (preferably less than 350) except in the presence of a surface active agent.

The invention further provides pharmaceutical compositions containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical composition according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following:

(a) fillers and extenders, e.g. starch, sugars, mannitol, and silicic acid;

(b) binding agents, e.g. carboxymethyl cellulose and other cellulose derivatives, alginates, gelatine and polyvinyl pyrrolidone;

(c) moisturizing agents, e.g. glycerol;

(d) disintegrating agents, e.g. agar-agar, calcium carbonate and sodium bicarbonate;

(e) agents for retarding dissolution e.g. paraffin;

(f) resorption accelerators, e.g. quaternary ammonium compounds;

(g) surface active agents, e.g. cetyl alcohol, glycerol monostearate;

(h) adsorptive carriers, e.g. kaolin and bentonite;

(i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in micro-encapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters (e.g. $C_{14}$-alcohol with $C_{16}$-fatty acid)) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example ground nut oil), glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5% usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 2.5 g to 10 g of active ingredient.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above-mentioned diseases in human and non-human animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), rectally or locally, preferably parenterally, especially intravenously. Topical application is possible, too. Preferred pharmaceutical compositions and medicaments are therefore those adapted for administration such as parenteral administration. Administration in the method of the invention is preferably parenteral administration.

In general it has proved advantageous to administer amounts of from 10 mg to 300 mg/kg, preferably 50 mg to 200 mg/kg, of body weight per day to achieve effective results. Nevertheless, it can at times be necessary to deviate from those dosage rates, and in particular to do so as a function of the nature and body weight of the subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

The following Examples 1 to 11 illustrate processes for the production of compounds of the present invention.

EXAMPLE 1

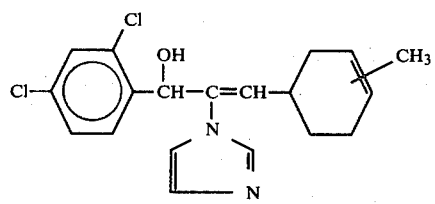
(I)

3.05 g (0.025 mole) of calcium chloride were added to 18.1 g (0.05 mole) of 1-(2,4-dichlorophenyl)-2-(imidazol-1-yl)-3-(methylcyclohex-3-en-1-yl)-2-propen-1-one in 100 ml of methanol, and the mixture was cooled to −20° C. 1.9 g (0.05 mole) of sodium borohydride were added in portions, and, when the addition had ended, the mixture was warmed to −10° C. Thereafter, an acetone/water mixture was added dropwise and the reaction mixture was allowed to warm to room temperature. It was adjusted to a pH value of 5 with dilute hydrochloric acid and concentrated. The residue was taken up in a mixture of methylene chloride/water and the organic phase was separated off, dried over sodium sulphate, filtered and concentrated. 15.6 g (85.7% of theory) of 1-(2,4-dichlorophenyl)-2-(imidazol-1-yl)-3-(methyl-cyclohex-3-en-1-yl)-2-propen-1-ol were obtained as an amorphous powder.

Preparation of the starting material

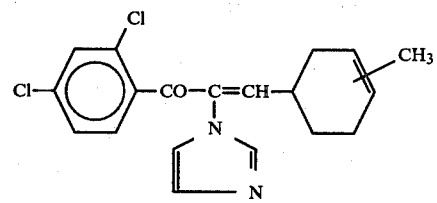

19.1 g (0.075 mole) of 2,4-dichlorophenacylimidazole, 9.3 g (0.075 mole) of methylcyclohexenealdehyde, 1.83 g (20 mole %) of benzoic acid and 0.96 g (15 mole %) of piperidine were taken up in a mixture of 75 ml of cyclohexane and 50 ml of toluene, and the mixture was heated under reflux for one hour, using a water separator. After cooling the reaction mixture, it was washed with dilute sodium bicarbonate solution and twice with water and the organic phase was separated off, dried over sodium sulphate, filtered and concentrated. The oil which remained was degassed. 27 g (99% of theory) of 1-(2,4-dichlorophenyl)-2-(imidazol-1-yl)-3-(methylcyclophex-3-en-1-yl)-2-propen-1-one were obtained as a viscous oil.

The following compounds of the general formula (I)

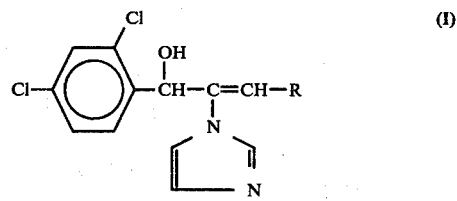

could be obtained analogously:

| Example No. | R | Physical constants |
|---|---|---|
| 2 | —⟨cyclohexenyl⟩ | amorphous |
| 3 | —CH(C₂H₅)₂ | amorphous |
| 4 | —CH(CH₃)—C₃H₇—n | amorphous |
| 5 | —CH₂—CH(CH₃)—⟨cyclohexyl-CH₃⟩ | amorphous |
| 6 | —CH(C₂H₅)—C₄H₉—n | amorphous |
| 7 | —C₆H₁₃—n | amorphous |
| 8 | —CH(CH₃)—⟨phenyl⟩ | amorphous |
| 9 | —CH(CH₃)—C₂H₅ | amorphous |

-continued

| Example No. | R | Physical constants |
|---|---|---|
| 10 | —⟨phenyl⟩—Cl | amorphous |
| 11 | —C₂H₅ | viscous oil |

The antimycotic activity of the compounds of this invention is illustrated by the following biotest Example.

In this Example, the compounds according to the present invention are each identified by the number (given in brackets) of the corresponding preparative Example, which will be found above in this specification.

The known comparison compound is identified as follows:

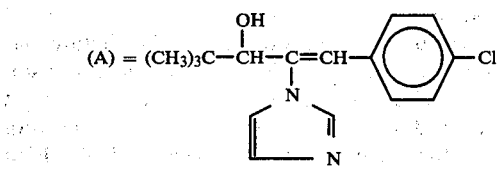

(a compound known from DE-OS (German Published No.) 2,838,847).

EXAMPLE A

Antimycotic in vitro activity

Description of the experiment:

The in vitro tests were carried out in a series dilution test with germ inocula of on average $5 \times 10^4$ germs/ml of substrate. The nutrient medium used was (a) for dermatophytes and moulds: Sabouraud's milieu d'epreuve and (b) for yeasts: meat extract/glucose broth.

The incubation temperature was 20° C. and the incubation period was 24 to 96 hours.

In this test, the tested compounds exhibited a better antimycotic action than the compound (A) which is known from the state of the art.

The present invention also comprises pharmaceutically acceptable bioprecursors of the active compounds of the present invention.

For the purposes of this specification the term "pharmaceutically acceptable bioprecursor" of an active compound of the invention means a compound having a structural formula different from the active compound but which nonetheless, upon administration to an animal is converted in the patient's body to the active compound.

What is claimed is:

1. A compound which is a substituted 2,4-dichlorophenyl-imidazolyl-vinyl carbinol of the formula

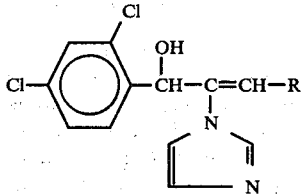

or a salt thereof,
in which
R represents a cycloalkyl or cycloalkenyl radical which has in each case 5 to 7 carbon atoms and is optionally substituted by alkyl with 1 to 4 carbon atoms; a cycloalkyl-alkyl or cycloalkenylalkyl radical which has in each case 5 or 7 carbon atoms in the cycloalkyl or cycloalkenyl part and in each case 1 to 6 carbon atoms in the straight-chain or branched alkyl part and is optionally substituted by alkyl with 1 to 4 carbon atoms; an optionally substituted straight-chain or branched alkenyl or alkinyl radical with in each case up to 6 carbon atoms, the substituents being selected from: hydroxyl, alkoxy with 1 to 4 carbon atoms, and phenyl, which is optionally substituted by halogen or alkyl with 1 to 4 carbon atoms; phenyl substituted by phenoxy or chlorophenoxy; or optionally substituted phenylalkyl radical with 1 to 4 carbon atoms in the alkyl part in the racemic form and/or in the form of the geometric and/or optical isomers.

2. A compound according to claim 1, in which R represents an optionally substituted phenylalkyl radical with 1 to 4 carbon atoms in the alkyl part, substituent(s) on the phenyl being selected from: halogen, alkyl with 1 to 4 carbon atoms and halogenoalkyl which has 1 to 2 carbon atoms and 1 to 5 identical or different halogen atoms, and substituent(s) on the alkyl being selected from; cyano, hydroxycarbonyl and alkoxycarbonyl with 1 to 4 carbon atoms in the alkyl part.

3. A compound according to claim 2, in which the phenylalkyl radical is a benzyl or 1-phenyl-eth-1-yl radical.

4. A compound according to claim 1, in which R represents an optionally methyl- or ethyl-substituted cyclohexyl, cyclohexenyl, cyclopentenyl, cyclopentyl, cyclohexyl-methyl, cyclohexyl-ethyl, 2-cyclohexyl-prop-1-yl, cyclohexenyl-methyl, cyclohexenyl-ethyl or 2-cyclohexenyl-prop-1-yl; methacryl, trimethylvinyl, acetylenyl, hydroxyacetylenyl, methoxyacetylenyl, phenacetylenyl, chlorophenylacetylenyl, propargyl, hydroxypropargyl, methoxypropargyl, phenylpropargyl or chlorophenylpropargyl radical; a phenyl radical which is substituted by phenoxy, or chlorophenoxy; or a benzyl or 1-phenyl-eth-1-yl radical which is optionally substituted in the phenyl part by fluorine, chlorine or methyl, and is optionally substituted on the methyl or ethyl group, respectively, by cyano or hydroxy- or methoxy-carbonyl.

5. A compound according to claim 1 which is 1-(2,4-dichlorophenyl)-2-(imidazol-1-yl)-3-(methyl-cyclohex-3-enlyl)-2-propen-1-ol.

6. A compound according to claim 1 which is 1-(2,4-dichlorophenyl)-2-(imidazol-1-yl)-3-(cyclohex-3-enlyl)-2-propen-1-ol.

7. A compound which is 1-(2,4-dichlorophenyl)-2-(imidazol-1-yl)-4-ethyl-2-hexen-1-ol.

8. The compound which is 1-(2,4-dichlorophenyl)-2-(imidazol-1-yl)-2-penten-1-ol.

9. An antimycotic pharmaceutical composition containing as an active ingredient an antimycotically effective amount of a compound according to claim 1 in admixture with an inert pharmaceutical carrier.

10. A pharmaceutical composition of claim 9 in the form of a sterile or physiologically isotonic aqueous solution.

11. A composition according to claim 9 or 10 containing from 0.5 to 95% by weight of the said active ingredient.

12. An antimycotic medicament in dosage unit form comprising an antimycotically effective amount of a compound according to claim 1.

13. A medicament of claim 12 in the form of tablets, pills, dragees, capsules, ampoules, or suppositories.

14. A method of combating mycoses in warm-blooded animals which comprises administering to the animals an antimycotically effective amount of an active compound according to claim 1 either alone or in admixture with a diluent or in the form of a medicament.

15. A method according to claim 14 in which the active compound is administered in an amount of 10 to 300 mg per kg body weight per day.

16. A method according to claim 14 or 15 in which the active compound is administered parenterally.

* * * * *

UNITED STATES PATENT AND TRADEMARK OFFICE
CERTIFICATE OF CORRECTION

PATENT NO. : 4,381,310
DATED : April 26, 1983
INVENTOR(S) : Wolf Reiser et al

It is certified that error appears in the above-identified patent and that said Letters Patent is hereby corrected as shown below:

| | |
|---|---|
| Col. 10, line 8 | Delete " -" between "methyl" and "cyclohex-" |
| Col. 10, line 34 | Delete "clophex" and insert --clohex-- |
| Col. 12, line 65 | After "3-" delete "enlyl" and insert --en-1-yl-- |
| Col. 12, line 67 | After "3-" delete "enlyl" and insert --en-1-yl-- |

Signed and Sealed this

Thirteenth Day of December 1983

[SEAL]

Attest:

GERALD J. MOSSINGHOFF

Attesting Officer

Commissioner of Patents and Trademarks